United States Patent [19]

Lowe

[11] 4,302,593

[45] Nov. 24, 1981

[54] INTERMOLECULAR COMPOUNDS OF AMINO ACIDS AND SULFOXIDES AND METHOD OF PREPARING SAME

[76] Inventor: Orville G. Lowe, 120-D W. Santa Fe Ave., Santa Fe, N. Mex. 87501

[21] Appl. No.: 135,663

[22] Filed: Mar. 31, 1980

Related U.S. Application Data

[63] Continuation-in-part of Ser. No. 869,811, Jan. 16, 1978, abandoned, which is a continuation-in-part of Ser. No. 653,517, Jan. 29, 1976, abandoned, which is a continuation-in-part of Ser. No. 532,722, Dec. 13, 1974, Pat. No. 3,948,922, which is a continuation-in-part of Ser. No. 320,070, Jan. 2, 1973, abandoned.

[51] Int. Cl.$^3$ .................. C07D 333/48; C07C 143/15
[52] U.S. Cl. ................................. 549/29; 260/513 N; 260/513 R; 549/28
[58] Field of Search ....................... 260/513 N, 513 R; 549/29, 87, 28

[56] References Cited

U.S. PATENT DOCUMENTS 3,428,671 2/1969 Toland ............................ 260/513 N
3,683,014 8/1972 Yang ................................ 260/513 N

*Primary Examiner*—Natalie Trousof
*Assistant Examiner*—Vera C. Clarke
*Attorney, Agent, or Firm*—John H. Crowe

[57] ABSTRACT

An intermolecular compound of an amino acid containing a sulfonic acid group and a carboxylic acid group with a sulfoxide in which the amino acid is at least moderately soluble.

A method which comprises reacting an amino acid containing a sulfonic acid group and a carboxylic acid group with a sulfoxide in which the amino acid is at least moderately soluble.

A method for recovering an amino acid containing a sulfonic acid group and a carboxylic acid group from an admixture of the amino acid with other ingredients by adding thereto a sulfoxide in which the amino acid is moderately soluble, with the sulfoxide being added in a sufficient amount to solubilize the amino acid, separating an intermolecular compound of the amino acid with the sulfoxide, and then recovering the amino acid from its intermolecular compound.

A method for forming an intermolecular compound of a sulfoxide with an amino acid containing a sulfonic acid group and a carboxylic acid group by contacting the amino acid with a solvent which contains the sulfoxide dissolved therein with the solvent having a low polarity and the amino acid reactant and intermolecular compound having a low solubility in the solvent. This method also provides a means for removing a sulfoxide from a solvent in which it is dissolved.

15 Claims, No Drawings

INTERMOLECULAR COMPOUNDS OF AMINO ACIDS AND SULFOXIDES AND METHOD OF PREPARING SAME

CROSS REFERENCE TO RELATED APPLICATIONS

This application is a continuation-in-part of United States application Ser. No. 869,811, filed Jan. 16, 1978, now abandoned, which is a continuation-in-part of United States application Ser. No. 653,517, filed Jan. 29, 1976, now abandoned, which was in turn a continuation-in-part of United States application Ser. No. 532,722, filed Dec. 13, 1974, now U.S. Pat. No. 3,948,922, which in turn was a continuation-in-part of United States application Ser. No. 320,070, filed Jan. 2, 1973, and now abandoned.

Dimethyl sulfoxide and related sulfoxides are known oxidizing agents. For example, as described in U.S. Pat. No. 3,428,671, lower dialkyl sulfoxides have been employed to oxidize a mercaptan to a sulfonic acid in the presence of a minor amount of bromide ion as a catalyst.

A sulfoxide, such as dimethyl sulfoxide, is relatively unstable. Thus, when used as an oxidizing agent, a substantial amount of the sulfoxide may undergo decomposition to form degradation products such as polyformaldehyde (also known as paraformaldehyde).

In investigating the usage of a sulfoxide as an oxidizing agent for production of sulfonic acids from thiols or disulfides, I have found that the sulfoxide may be satisfactorily employed as an oxidizing agent under certain conditions. In general, these conditions entail heating a solution of the thiol or disulfide reactant in the sulfoxide, i.e., the thiol or disulfide reactant being at least moderately soluble in the reaction mixture, in the presence of a moderating excess of water and a halogen or hydrogen halide catalyst (the hydrogen halide forming a hydrohalic acid in the presence of water). The halogens or hydrogen halide catalysts which may be employed are iodine, bromine, chlorine, hydrogen iodide, hydrogen bromide, hydrogen chloride or mixture thereof. This, therefore, includes all of the halogens and hydrogen halides with the exception of fluorine and hydrogen fluoride.

The oxidation process may be illustrated by the following generalized reactions:

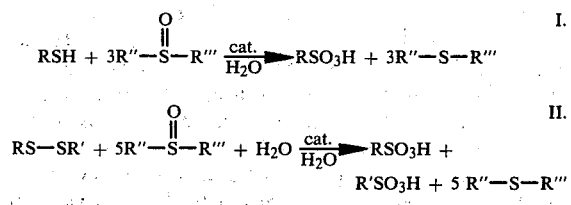

In the above equations, R and R' may be either aliphatic cycloaliphatic, aromatic, or heterocyclic groups such as methyl, ethyl, 1-bicyclo (2,2,2)octyl, isopropyl, n-pentyl, cyclohexyl, phenyl, benzyl, tolyl, pyridyl, imidazoyl, thiazolyl, dibenzofuranyl, and the like. When R or R' are aliphatic or cycloaliphatic groups, they preferably contain from one to about twenty carbon atoms and when R or R' are aromatic or heterocyclic groups (either aromatic or saturated), they preferably contain from about five to about twenty carbon atoms. When the groups R and R' are aromatic or cyclic, they may be either monocyclic or polycyclic. When both R and R' are present in a disulfide reactant, they may be the same or different. In addition, —SR' may be a sulfonate group such as —SO$_3$Na, —SO$_3$NH$_4$, or —SO$_3$K, or the sulfonic acid group —SO$_3$H. In this instance, the reactant RS—SR' will have the formula RS—SO$_3$Z in which Z is hydrogen or a monovalent cation.

R and R' are preferably free from olefinic or acetylenic unsaturation, e.g., they are saturated or their unsaturation is of aromatic character. Also, R and R' may include substituent groups which are unreactive under the conditions of the process, e.g., amino (preferably in the ammonium form), carbonyl, nitro, carboxylic acid groups, and the like or R and R' may be substituted with additional thiol groups so that RSH represents, e.g., a dithiol reactant to produce a disulfonic acid product. Preferably, the carbon atom in the groups R or R' which is bonded to sulfur is not a tertiary carbon atom, i.e., a carbon atom which is bonded to three other carbon atoms and also to sulfur as in the case of 2-methyl-2-propanethiol or bis(t-butyl) disulfide since these groups favor decomposition of the thiol or disulfide reactant.

When R or R' is an aromatic heterocyclic group, its degree of aromaticity is preferably of the order of benzene. Basic heterocyclic groups are preferably present in the salt from e.g., pyridium, and the like. Preferably, substituent groups or the aromatic heterocyclic group are electron withdrawing or meta directing groups such as ammonium, nitro, or cyano or a carbonyl containing group such as carboxyl.

The groups denoted as R" and R"' in the above equations are lower alkyl groups such as methyl, ethyl, isopropyl and the like. R" and R"' may be either the same or different and may be bonded together to form a ring structure, as in the case of tetramethylene sulfoxide. As shown, a reaction product which results from my process is a sulfide in which R" or R"' may each be bonded to a sulfur atom. The volatility of the resulting sulfide is dependent upon the size of the groups R" and R"'. Desirably, the resulting sulfide is relatively volatile and, thus, it is preferable that R" and R"' are relatively small groups, such as methyl groups. In this case, the resulting sulfide is dimethyl sulfide which has a boiling point of 38° C. and it is readily removed from the reaction mixture through distillation.

As illustrated, water is not a reactant in the oxidation of a thiol to form a sulfonic acid (Equation I) but is a reactant in the oxidation of disulfide to form a sulfonic acid (Equation II). In both of the reactions I and II, water is present, however. In the oxidation of a thiol, the water is present in an amount sufficient to moderate the oxidation and to inhibit degradation of the sulfoxide reactant to form unwanted decomposition products such as polyformaldehyde. Generally, the quantity of water employed in the reaction shown in Equation I will be in the order of about one-half to about one mole for each mole of the thiol reactant. By reason of the stoichiometry of the reaction shown in the Equation II, the quantity of water employed will generally range in excess of about one to about two moles of water for each mole of the disulfide reactant. The water content of the reaction mixture may be substantially in excess of the mole of water for each mole of thiol reactant or two moles of water for each mole of disulfide reactant. As the water content is increased, the solubility of some thiol or disulfide reactant (depending on the presence or absence of water-solubilizing substituents) may be reduced to some extent and the reaction rate, thereby, slowed. If the reaction rate becomes slower than desired (for whatever reason), then the reaction may be considered over moderated and the water content can be reduced. In general, the water content will not exceed about 20% by weight of the reaction mixture.

In demonstrating the effect of the excess water on the above-described oxidation reaction, it was found that the reaction of dimethyl disulfide in solution in dimethyl sulfoxide using one mole of water for each mole of the disulfide reactant and hydrogen bromide as a catalyst produced an abundant amount of polyformaldehyde at a reaction temperature of 90° C. However, when the reaction was conducted under identical conditions using 1.45 moles of water for each mole of dimethyl disulfide, only trace amounts of polyformaldehyde were formed.

Similarly, when benzenethiol was reacted with dimethyl sulfoxide at 110° C., the reaction was very rapid and vigorous and produced an abundant quantity of polyformaldehyde. However, when the reaction was conducted under identical conditions in the presence of 0.71 moles of water for each mole of benzenethiol, the nature of the reaction was moderate and no polyformaldehyde was detected.

As stated previously, the catalyst employed in the oxidation process may be either a halogen or a hydrogen halide. It is believed that the halogen and hydrogen halide are interchangeable as catalysts because a reversible reaction is believed to take place between a sulfoxide, such as dimethyl sulfoxide, and a hydrogen halide as shown in the following equation:

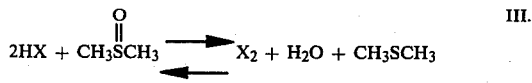

$$2HX + CH_3\overset{\overset{O}{\|}}{S}CH_3 \rightleftharpoons X_2 + H_2O + CH_3SCH_3 \qquad \text{III.}$$

"X" in the above Equation III is iodine, bromine, or chlorine. Iodine and hydrogen bromide are preferred catalysts for use in my process. Hydrogen chloride was not found to be as effective a catalyst; however, hydrogen chloride was found to be an extremely effective catalyst when there was a trace of another halogen, particularly iodine, present.

In carrying out my work, a convenient satisfactory thiol concentration has been about 2.4 moles or less of the thiol for each liter of the sulfoxide, such as dimethyl sulfoxide. In the case of the disulfide oxidation, a convenient and satisfactory concentration of the disulfide reactant has been about 1.2 moles or less of the disulfide for each liter of the sulfoxide. Using these concentrations of the thiol or disulfide reactant, I have found a convenient water concentration to be 1.11 moles of water per liter of the sulfoxide for oxidation of a thiol and 2.22 moles of water per liter of sulfoxide for oxidation of a disulfide. On a volume basis, this corresponds to about 2% by volume of water for the thiol oxidation and about 4% by volume of water for the disulfide oxidation.

As stated, the presence of excess water, which is essential to the oxidation process, has been found to have a moderating effect. As the content of water is increased, there is a tendency for the rate of the oxidation reaction to slow. As the excess quantity of water is reduced, the oxidation reaction becomes more rapid but there is also a greater probability that undesirable decomposition of the sulfoxide will occur. In all cases, a certain excess of water will be present in the reaction mixture. However, depending upon the particular reaction involved, the excess quantity of water may be reduced to accelerate the oxidation reaction. Since the decomposition of the sulfoxide is dependent upon the reaction temperature, as the quantity of excess water is reduced, the reaction temperature may also be reduced to control the undesired decomposition of the sulfoxide reactant within reasonable limits.

To illustrate the effect of the water concentration upon the oxidation reaction, when dimethyl disulfide was oxidized in dimethyl sulfoxide at 130° C. using iodine catalysis, the reaction was completed in about 4¼ hours when 2.22 moles of water were present for each liter of dimethyl sulfoxide. When the reaction was repeated using 4.44 moles of water for each liter of dimethyl sulfoxide, the reaction time was increased to five hours in order to obtain completion. Similarly, when dimethyl disulfide was oxidized in dimethyl sulfoxide at 90° C. using hydrogen bromide catalysis, only a negligible amount of reaction occurred when 2.22 moles of water were present for each liter of dimethyl sulfoxide. However, when the reaction was repeated and the water content was reduced to 1.62 moles of water for each liter of dimethyl sulfoxide, the reaction was completed in about 10¾ hours.

As in the case of the excess water which is required, the catalyst content in the reaction mixture may be varied in the performance of the process. As the catalyst content is increased, the reaction time is decreased while a decrease in the catalyst content results in an increase in reaction time. A convenient catalyst concentration, which I have employed in certain of my experiments, is about 0.035 moles of the hydrogen halide catalyst for each liter of the sulfoxide reactant, or 0.035 gram atoms of halogen per liter of the sulfoxide reactant. For simplification, the concentration of halogen is described in terms of hydrogen halide equivalents, i.e., 0.035 gram atoms/liter equals 0.035 molar as hydrogen halide equivalent. When using iodine in conjunction with hydrochloric acid as the catalyst, a molarity of 0.0064 hydrogen iodide equivalents for the iodine and 0.035 molar for the hydrogen chloride has proven to be satisfactory.

Since an increase in the excess water concentration in the reaction mixture serves to moderate the oxidation reaction and to control the undesired decomposition of the sulfoxide reactant, the content of excess water may be increased in conjunction with an increase in the catalyst level. Thus, as the reaction rate is increased by increasing the catalyst level, the level of excess water may be increased to control the undesired dimethyl sulfoxide decomposition at the increased reaction rate. It has been found that the concentration of excess water need not be increased in proportion to the increase in the catalyst concentration. Thus, beneficial results, such as a decrease in the reaction time or the obtaining of a comparable reaction time at a lower reaction temperature can be obtained.

In illustrating the effect of catalyst concentration with respect to reaction time, dimethyl disulfide was oxidized at a reaction temperature of 110°-120° C. using hydrogen bromide catalysis. When the catalyst concentration was 0.0178 molar, the reaction time was 6½ hours, whereas the reaction time was only 3¼ hours when the catalyst concentration was 0.0356 molar. Similarly, using iodine catalysis at 130° C., the reaction time was 6¼ hours with a catalyst concentration of 0.0158 molar as HI, and 4¼ hours for a catalyst concentration of 0.0316 molar as HI.

The effect on reaction time of changing both the water concentration and the catalyst concentration is illustrated in the following table in which dimethyl disulfide was oxidized in the presence of dimethyl sulfoxide. The concentration of both the water and hydrogen bromide catalyst is set forth in the table in terms of moles for each liter of dimethyl sulfoxide.

TABLE I

| Oxidation Temp. | Conc., H$_2$O | Conc., HBr | Reaction Time |
|---|---|---|---|
| 100 C. | 2.22 M | 0.0356 M | 6½ Hours |
| 100 C. | 3.33 M | 0.0712 M | 5 Hours |
| 90 C. | 2.22 M | 0.0356 M | Negligible Reaction |
| 90 C. | 4.44 M | 0.142 M | 6½ Hours |

As illustrated by the above table, the concentration of the excess water in the reaction mixture and also the concentration of the catalyst may be varied in the performance of my process to obtain optimum results. In particular, I have found that the use of relatively high catalyst concentrations, e.g., in excess of about 0.035 M as hydrogen halide and only moderately high water concentrations, e.g., in excess of about 1.0 M of water per liter of sulfoxide for oxidation of a thiol and in excess of about 2.0 M of water per liter of sulfoxide for oxidation of a disulfide, has been most useful where the sulfur compound undergoing oxidation also contains a basic group such as an amino group. An example of a sulfur-containing reactant which includes an amino group is L-cystine which will be discussed in more detail in Example VI and following.

In the catalysis of the oxidation reaction according to the process, I have found that there may be a secondary acid catalysis which is superimposed on the primary halogen-hydrogen halide catalysis. This is manifested by relatively slow reaction rate at the beginning and then an increase in the reaction rate as the acid content is increased due to formation of the sulfonic acid product. This effect can be used advantageously in my process by adding a strong acid that is essentially fully dissociated in aqueous solution for the first ionizable proton, i.e., a pK equaling about zero for the first ionization, before the start of the oxidation reaction. This permits a more even or controlled oxidation which may result in a shorter time to completion and possibly even at a lower temperature. Any strong acid such as sulfuric acid or a sulfonic acid may be employed. While the concentration of the strong acid which is added may be varied depending upon the specific reaction involved, suitable quantities of the added acid may range from about 0.08 to about 0.4 moles per liter of the sulfoxide reactant, e.g., dimethyl sulfoxide. In order to simplify the separation procedures for recovery of the desired sulfonic acid product, it is preferred to use as the added strong acid the sulfonic acid which is the desired reaction product.

To illustrate the effect of adding methanesulfonic acid, dimethyl disulfide was oxidized in dimethyl sulfoxide using iodine catalysis both with and without added methanesulfonic acid. When methanesulfonic acid was not added, the reaction was complete in 4¼ hours at 130° C. However, when 0.4 moles of methanesulfonic acid was added to the reaction mixture for each liter of dimethyl sulfoxide, the reaction was complete in five hours using a reaction temperature of only 110° C. When the reaction was attempted using hydrogen bromide catalysis, the reaction was negligible at 90° C. when methanesulfonic acid was not added. However, when methanesulfonic acid was added, the reaction was approximately one-third complete after seven hours at 90° C.

As described, the reaction temperature may be varied in carrying out the oxidation process depending upon the quantity of excess water, the catalyst concentration, the specific thiol or disulfide reactant, etc. In general, I have employed reaction temperatures ranging from about room temperature to as high as about 140° C. Generally, a temperature of about 110° C. was found to be quite satisfactory for hydrogen bromide catalysis while somewhat higher temperatures were found more suitable for iodine catalysis. Lower temperatures than 110° C. were often found suitable when the reaction was catalyzed by a combination of iodine or hydrogen bromide in conjunction with hydrogen chloride, or with the assistance of secondary acid catalysis, i.e., the addition of a strong acid before the start of the oxidation reaction.

In the performance of the process, the reactants are heated in a vessel which may be equipped with a distillation head. When using dimethyl sulfoxide as the oxidant, the sulfide produced by the reaction is dimethyl sulfide which has a relatively low boiling point of 38° C. As the dimethyl sulfide was formed, it was allowed to distill off. In order to obtain reaction economies, the dimethyl sulfide, or other sulfide in the case where the sulfoxide reactant is not dimethyl sulfoxide, may be reoxidized and recycled to the process. Any desired means for reoxidizing the sulfide may be employed. By way of illustration, if the sulfide formed is dimethyl sulfide, it may be reoxidized to dimethyl sulfoxide by catalystic air oxidation.

There may be some tendency for a specific sulfonic acid product to undergo further oxidation to form sulfuric acid. In controlling this undesirable reaction, I have found it desirable to lower the reaction temperature where this is a problem.

After the oxidation reaction is completed, i.e., generally indicated by a reduction in the rate of sulfide formation or evolution from the reaction mixture, the sulfonic acid product may be recovered directly by any suitable means. For example, the product may be separated from excess sulfoxide reactant, e.g., dimethyl sulfoxide, by ion exclusion chromatography.

In view of the relatively low melting point and relatively high solubility of most sulfonic acids, the reaction mixture may be neutralized by the addition of an aqueous base such as aqueous sodium hydroxide solution and the product separated in the form of its salt. The salt may then be the desired product or an acid product may be obtained by acidifying the salt. In precipitating the desired product as the sodium sulfonate from the neutralized mixture, I have found it convenient to add a mixture of acetone and ethyl acetate with crystallization of the salt from alcohol.

To further illustrate the invention, there are presented the following examples in which all parts and percentages are by weight unless otherwise indicated.

EXAMPLE I

A solution of 15 ml of dimethyl disulfide (DMDS) (168.9 mmol), 6 ml of water (333 mmol), and 0.6 ml of concentrated hydrobromic acid (5.34 mmol) in 150 ml of dimethyl sulfoxide (DMSO) was heated at 100° to 110° C. in a 250 ml flask equipped with a distillation head. After a period, a distillation at 38° to 45° C. commenced. Heating was continued until the distillation temperature dropped and distillation slowed to less than one ml in a 15-minute period (about 4¼ hours). Fifty-six and one-half (56½) ml of distillate was obtained. This proved to be mainly dimethyl sulfide (DMS). It redistilled at 37°-39° C. (reported, 38°) and gave a mercuric chloride derivative melting at 159°-61° C. (reported, 156°-8°).

Two-thirds of the reaction mixture was removed and, after dilution with 200 ml of water, the acid product was separated from excess DMSO by ion exclusion chromatography on Dowex ion exchange resin (50-X8, acid form). The acid fraction was concentrated, then methanesulfonic acid distilled at 129°-32°/1 mm (reported, 122°/1 mm). There was obtained 19.56 g. (90% yield) with an Mp of 16°-18° (reported, 20°). Neutralization equivalent, 97.3 (calculated, 96.1).

The remaining third of the reaction mixture was neutralized by addition of 24.3 ml of 5 N sodium hydroxide solution. Two hundred fifty ml of acetone and 150 ml of ethyl acetate were added to produce a precipitate. This precipitate (12.42 g after drying at 130°, which was a 93% yield of crude sodium methanesulfonate) was crystallized from 95% alcohol. Mp, 353°-5° (reported, 345°). Treatment with phosphorous pentachloride and then ammonia yielded the amide, Mp 89°-92° C. (reported, 90° C.).

Many additional oxidations of DMDS to a methanesulfonic acid were undertaken. Generally, DMDS was oxidized at a concentration of 1.126 M in dimethyl sulfoxide. At double this concentration, 2.252 M, the oxidation was more difficult to control. With HBr as the catalyst (0.0356 M) and water at 2.22 M, the oxidation went to completion in about 3¼ hours at 110° C. At 100° C. more than 6½ hours were required, and at 90° C. there was negligible reaction. However, oxidation was obtained at 90° C. by adding methanesulfonic acid or by decreasing the water concentration. With 0.4 M methanesulfonic acid present initially, the oxidation was one-third complete in seven hours at 90° C. and may have gone to completion in about fourteen hours, and with 1.62 M water, the oxidation was complete in 10¾ hours at 90° C. At 80° C. there was little reaction even with 1.134 M water unless methanesulfonic acid was added. On the other hand, the oxidation went to completion in 6½ hours at 90° C. with 0.1424 M HBr and 4.44 M water.

With iodine as the catalyst (0.0316 M as HI equivalents), 130° C. was the preferred temperature (DMDS 1.126 M as above and water 2.22 M), the oxidation going to completion in 4¼ hours. On addition of methanesulfonic acid to a concentration of 0.4 M, the oxidation went to completion in five hours at 110° C. With a mixed HCl—$I_2$ catalyst (0.036 M as HI equivalents, respectively), the oxidation went to completion in 6¼ hours at 100° C.

Methanesulfonic acid was obtained in 93 to 97% yield based on recovered crude sodium methanesulfonate. Recrystallization of this salt from 95% alcohol gave small needles, Mp was 353°-355° C. Reported Mp, 345° C. The amide derivative melted at 89°-92° C. (reported Mp, 90° C.).

Diethyl disulfide was also oxidized to ethanesulfonic acid in dimethyl sulfoxide with the use of $I_2$ or HBr as a catalyst. One hundred twenty degrees (120) was the preferred temperature for the iodine catalyzed oxidation. At a concentration of 0.972 M with an iodine concentration of 0.0316 M (HI equivalents) and water 2.22 M, diethyl disulfide was oxidized in six hours. After neutralization, the crude sodium sulfonate was obtained in 84% yield with correction for the sodium sulfate ($Na_2SO_4$) that was present, (i.e., $Na_2SO_4$ removed by recrystallization of the product from abolute alcohol).

The HBr catalyzed oxidation of diethyl disulfide was carried out at 110° C. With the same concentration as above except for a concentration of 0.0356 M HBr catalyst, the oxidation was complete in 3¾ hours. The yield as the crude sodium sulfonate salt after neutralization was 82% with correction for $Na_2SO_4$. The oxidation of diethyl disulfide produced more $H_2SO_4$ than that of DMDS. The yields of $H_2SO_4$ were 8% with $I_2$ catalysis and 0.6% with HBr catalysis.

Recrystallization of the crude sodium ethanesulfonate from absolute alcohol gave matted crystals which melted at about 260° C. in an evacuated capillary. The amide derivative melted at 57½° to 60½° C. (reported Mp, 60° C.).

Oxidations of 1-butane thiol to 1-butanesulfonic acid in dimethyl sulfoxide were undertaken with this thiol at a concentration of 1.85 M and water at 1.11 M. The $I_2$ catalyzed reaction (0.0316 M as HI equivalents) was carried out at 120° C. for seven hours. The yield of the product as crude sodium salt corrected for $Na_2SO_4$ was 71%. $Na_2SO_4$ yield was 20%.

The HBr catalyzed reaction of 1-butane thiol (0.0356 M HBr) was carried out at 110° C. for 5¾ hours and the product yield as crude sodium salt corrected for $Na_2SO_4$ was 89%. $Na_2SO_4$ yield was 4%.

Recrystallization of the crude sodium 1-butanesulfonate from absolute alcohol gave matted crystals. On heating in an evacuated capillary, these sintered at about 250° C. without complete melting (taken to 290°). The amide derivative melted at 42½° to 45½° C. (reported Mp, 45°).

2-Propanethiol, which is a secondary thiol, was oxidized in dimethyl sulfoxide at a concentration of 1.69 M. Water was 1.11 M. A HBr catalyzed reaction (0.0357 M HBr) was conducted at 110° C. though initially a lower temperature (70° to 100° C.) was used to avoid boiling off of this volatile thiol. Ten and three-fourths hours were required to complete the oxidation and there was obtained a 90% yield of the crude sodium salt (corrected for $Na_2SO_4$ of which there was a 2.4% yield).

Mixed HCl—$I_2$ catalyzed reactions of 2-propanethiol were also carried out in dimethyl sulfoxide. The preferred temperature was 110° C. though initially a lower temperature was again used. With HCl as 0.036 M and $I_2$ as 0.0065 M as HI equivalents, 20 hours were required to complete the oxidation. There was obtained a 44% yield of the crude sodium salt (corrected for $Na_2SO_4$ of which there was a 45% yield). This was an instance in which HCl—$I_2$ catalysis did not work as well as HBr catalysis.

The crude sodium 2-propanesulfonate was recrystallized from 95% alcohol. It did not melt below 360°. The amide derivative melted at 59°-62° C. (reported Mp, 60° C.).

EXAMPLE II

A solution of 8 ml of benzenethiol (78.4 mmol), 1 ml of water (55.5 mmol), and 0.2 g of iodine (1.59 mmol as HI equivalents) in 50 ml of DMSO was heated at 130° C. in a 100 ml flask equipped with a distillation head for 4¾ hours. During this time a distillation at 37° to 45° C. occurred but eventually slowed to less than ⅛ ml in a 15-minute period. 14.7 ml of distillate (DMS) were obtained. After cooling, the reaction mixture was neutralized by addition of 16.9 ml of 5 N sodium hydroxide solution. There was added 225 ml of acetone and 175 ml of ethyl acetate to produce a precipitate. On removal of this, concentration of its filtrate by boiling until a temperature of 110° C. was reached, and then adding 200 ml of ethyl acetate, a second precipitate was produced. These precipitates were combined and dried at 130° C. to give 12.26 g of crude sodium benzenesulfonate (87% yield). Crystallization from alcohol gave matted flakes. Treatment with phosphorous pentachloride, then ammonia yielded the amide, Mp 155°–7° C. (reported, 153°).

Diphenyl disulfide was similarly oxidized to benzene sulfonic acid using a disulfide concentration of from 0.548 to 0.732 M and doubling the water concentration to about 2.22 M. Iodine catalyzed reactions (0.0316 M as HI equivalents) were conducted at 130° C.; and HBr catalyzed reactions (0.0356 M HBr), at 110° C. Iodine catalysis required about 3¾ hours for oxidation of the disulfide and HBr catalyzed reactions required about 3½ hours for completion.

Yields of the crude sodium salt ranged from 84 to 94%. There was negligible $Na_2SO_4$ and recrystallization from alcohol gave matted flakes. The Mp of the amide derivative was 155°–7° C. (reported Mp, 153° C.).

EXAMPLE III

A mixture of 8 g of bis (2-nitrophenyl) disulfide (26.0 mmol), 1 ml of water (55.5 mmol), 0.4 ml of concentrated hydrobromic acid (3.56 mmol), and 50 ml of DMSO was heated in a 100 ml flask equipped for distillation. Heating was started at 120° C., then the temperature was gradually allowed to drop to about 106° C. A distillation at 40° to 42° set in. This had slowed but was still continuing at 7 hours when heating was discontinued. There was obtained 11.2 ml of distillate (DMS). The reaction mixture was neutralized by the addition of 15.2 ml of 5 N sodium hydroxide solution. Water was then removed under vacuum through use of a rotating evaporator. The residue was triturated with 200 ml of ethyl acetate and then again, with 100 ml of fresh ethyl acetate giving 10.89 g of crude sodium 2-nitrobenzenesulfonate after drying at 130° C. Crystallization from 95% alcohol removed 0.33 g of insoluble sodium sulfate. The crude yield of the product corrected for this $Na_2SO_4$ was 90%. Treatment of the recrystallized product with phosphorous pentachloride followed by ammonia yielded the amide having a Mp of 191°–4° C. (reported, 193° C.).

Oxidation of bis (2-nitrophenyl) disulfide is the usual route to 2-nitrobenzenesulfonic acid. For this reason, its oxidation by DMSO was investigated. A variety of conditions were explored and, in general, this disulfide resisted oxidation unless somewhat extreme conditions were used. These conditions entailed the use of lower water and higher catalyst concentrations than usual with the consequence that the limits of stability of DMSO were pressed. Hence, the oxidation was somewhat marginal with a high DMS yield and high base titer indicating the presence of methanesulfonic acid from decomposition of the DMSO, and possibly also the presence of sulfuric acid.

Moderately good results were obtained with this bis (2-nitrophenyl) disulfide at a concentration of 0.52 M in DMSO (not completely soluble), HBr at 0.0712 M, and water at 1.11 M. Oxidation was at 120° C., though the temperature could later be dropped. Four and one-half to seven hours were required and the yield of the crude sodium salt was 90% (corrected for $Na_2SO_4$). Sodium methanesulfonate was not isolated.

Recrystallization of the crude sodium 2-nitrobenzenesulfonate from 95% alcohol gave small flakes. These melted at 289°–92° C. with decomposition. The amide melted at 191°–4° C. (reported Mp, 193° C.).

EXAMPLE IV

A mixture of 10.0 g of bis(2-naphthyl) disulfide (31.4 mmol), 2 ml of water (111 mmol), 0.15 ml of concentrated hydrochloric acid (1.8 mmol), 41.1 mg of iodine (0.32 mmol as HI equivalents), and 50 ml of DMSO was heated as usual at 100° to 105° C. for 4¼ hours. During this time a distillation at 35° to 42° C. occurred but eventually slowed to less than ¼ ml in a 15-minute period. There was obtained 11.0 ml of distillate (DMS). The reaction mixture was neutralized by the addition of 15.0 ml of 5 N sodium hydroxide solution and then treated with 150 ml of acetone and 250 ml of ethyl acetate. The precipitate was filtered off and the filtrate was concentrated by boiling until its temperature was 110° C. Addition of 300 ml of ethyl acetate produced a second precipitate. These precipitates were combined and dried at 130° C. to give 14.46 g of crude sodium 2-naphthalenesulfonate. Recrystallization from water gave 11.47 g, 79% yield. The amide was prepared by the usual route, Mp 215°–8½° C. (reported, 217° C.).

A further aspect of my invention concerns the preparation of intermolecular compounds of an amino acid containing a sulfonic acid group and a carboxylic acid group with a sulfoxide in which the amino acid is at least moderately soluble, i.e., a solubility of about 4.0 grams or more per 100 ml of the sulfoxide at a temperature of about 25° C. The sulfoxide may be of the type as previously described where R" and R'" are lower alkyl groups. Each alkyl group may contain up to about six carbon atoms which groups may be the same or different and may be bonded together to form a ring structure. Thus, the sulfoxide may be dimethyl sulfoxide, diethyl sulfoxide, dihexyl sulfoxide, methyl ethyl sulfoxide, methyl propyl sulfoxide, ethyl isopropyl sulfoxide, 2-butyl pentyl sulfoxide, tetramethylene sulfoxide, pentamethylene sulfoxide, or the like. The intermolecular compounds may contain the amino acid and the sulfoxide at a molar ratio of one-to-one and the intermolecular compound is usually obtained as a crystalline compound although it may be a heavy fluid depending upon the specific amino acid and specific sulfoxide which it contains.

The intermolecular compounds, as described, may be readily formed by dissolving a fair to moderate amount of the amino acid in the sulfoxide (either alone or in admixture with a diluent solvent for the amino acid) with stirring and gentle heating, if needed. The intermolecular compound may precipitate from the excess sulfoxide. However, it is preferred to add a solvent, to assist precipitation, which is moderately nonpolar, e.g., a dielectric constant between about 5 and about 26, which has a fair degree of solubility in the reaction mixture.

Typical of solvents found suitable for precipitating the intermolecular compounds are acetone, ethyl acetate and chloroform. Also, mixed solvents such as a mixture of dimethyl sulfide with acetone were found suitable.

Typical of amino acids which contain a sulfonic acid group and also a carboxylic acid group which may be used are cysteic acid, homocysteic acid which is 2-amino-4-sulfobutyric acid, 3-amino-4-sulfobutyric acid, 2-amino-3-sulfobutyric acid (both diastereoisomers), 3-amino-2-sulfobutyric acid (both diastereoisomers), 4-amino-2-sulfobutyric acid, 2-amino-2-methyl-3-sulfopropionic acid, 3-amino-2-methyl-2-sulfopropionic acid, isocysteic acid, and 4-amino-3-sulfobutyric acid. The amino acid may be the optically active D- or L-form or it may be racemic. In broader terms, the amino acid is a saturated aliphatic amino acid of the empirical formula $C_nH_{2n-1}(NH_2)(CO_2H)(SO_3H)$, wherein n is a small whole number from 1 to about 4, inclusive. Examples of the amino acid are L-cysteic acid, D-cysteic acid, DL-cysteic acid and DL-homocysteic acid.

The formation of the above-described intermolecular compounds may be used in order to separate or purify an amino acid containing a sulfonic acid group and a carboxylic acid. Thus, for example, the amino acid may be separated from a mixture of other materials by the addition thereto of a sulfoxide in which the amino acid goes into solution with the solution then being separated from the other ingredients in admixture with the amino acid. Following this, the amino acid may be recovered by precipitating the intermolecular compound from the sulfoxide, as described previously, and then liberating the amino acid from the intermolecular compound. One means of liberating the amino acid from the intermolecular compound is to heat the intermolecular compound at a moderately elevated temperature, e.g., about 90° to 130° C. and preferably under vacuum. As a result of the heating, the intermolecular compound will lose the sulfoxide to provide the purified amino acid.

A further way of recovering the amino acid from the intermolecular compound is to mix or triturate the intermolecular compound with a solvent such as methanol, acetonitrile or the like which is analogous to an extraction or leaching operation. The intermolecular compound is not completely dissolved although it may dissolve locally and then be immediately redeposited as the amino acid. Thus, anhydrous L-cysteic acid may be obtained in this manner as a relatively fine powder that is readily soluble in water. The solvents used for recovery of the amino acid from the intermolecular compound are preferably of moderate polarity, e.g., a dielectric constant of about 20 or greater and preferably about 25 or greater, so that they are generally able to effect the change to the amino acid but not dissolve the liberated amino acid. Methanol, ethanol and acetonitrile have been used successfully and, in general, the lower alcohols and ethylene glycol may be employed.

Depending on its sulfoxide component, certain of the above-described intermolecular compounds may be readily soluble in water which is a highly polar solvent, i.e., having a dielectric constant of about 80. Thus, for example, with the addition of L-cysteic acid-dimethylsulfoxide intermolecular compound to water, the solution eventually became saturated such that L-cysteic acid crystallized out. This is a further method of recovering the amino acid although it is not preferred because of the relatively high solubility of the amino acid in the polar solvent.

EXAMPLE V

One and one-tenth grams of L-cysteic acid monohydrate was treated with 4 ml of DMSO. It slowly dissolved with swirling and some heating. Five ml of acetone was then added with swirling. Toward the end of this addition, a crystallization set in. After a period, 2 ml more of acetone were added. Then, after cooling with ice, the crystalline product was filtered off. Obtained 1.37 g of L-cysteic acid-DMSO molecular compound (yield, 94%). This sintered at 160° C. then gradually decomposed on heating to 180° C.

The intermolecular compound of L-cysteic acid with dimethyl sulfoxide, as obtained from Example V, may be recrystallized by dissolving it in DMSO and then adding acetone.

The L-cysteic acid-DMSO intermolecular compound sintered at 160° C., gradually darkened, then decomposed at about 180° C. It was soluble in water. The dilute solution had a pH of about 2 and would rapidly reduce added potassium permanganate solution. The specific optical rotation $[\alpha]^{25}D$, of an 11% solution was +5.92°. Elemental analysis was in accord with the formula $C_5H_{13}O_6NS_2$.

|   | Calculated | Found |
|---|---|---|
| C | 24.28% | 24.64% |
| H | 5.30 | 5.40 |
| N | 5.67 | 5.45 |
| S | 25.93 | 26.03 |

The combination of properties—water solubility, acidity, positive optical rotation, reduction of permanganate—in conjunction with the elemental composition indicated that an intermolecular compound of L-cysteic acid with DMSO ($C_5H_{13}O_6NS_2=C_3H_7NO_5S.C_2H_6OS$) had been formed in which each component was manifesting its properties.

To further substantiate this, it was established that the product oxidized 57% hydriodic acid. Qualitative determination of the amount oxidized indicated the presence of 31.65% DMSO (theory for $C_3H_7NO_5S.C_2H_6OS$, 31.59%). When vacuum dried at 120° C., the product lost 31.86% of its weight (calculated for loss of DMSO from $C_3H_7NO_5S.C_2H_6OS$, 31.59%). The residual material, decomposed at 260°-3° and its aqueous solution had a pH of about 2.

When thoroughly and intimately mixed with methanol, ethanol or acetonitrile followed by removal of the solvent, the intermolecular compound lost about a third of its weight. The residue decomposed at about 270° C. (capillary inserted at 260°), and its aqueous solution had a pH of about 2 but would not readily reduce permanganate. On the other hand, the removed solvent readily reduced permanganate.

The residual product thus obtained proved to be anhydrous L-cysteic acid, reported Mp 274° C. (decomposition). It could be crystallized from water to give the monohydrate form, Mp 272°-4° (decomposition) (reported, 274° with decomposition); $[\alpha]D^{25}$, +8.45° (7.4% aqueous solution on the anhydrous basis) (reported, +8.66°); loss of weight on vacuum drying at 110° C., 9.36% (calculated for monohydrate, 9.62%).

The cysteic acid monohydrate could, in turn, be reconverted into the intermolecular compound by dissolving in DMSO and precipitating the intermolecular compound by the addition of acetone.

A similar intermolecular compound is obtained by using DL-cysteic acid in place of L-cysteic acid in the above example.

EXAMPLE VI

A mixture of 16 g of L-cystine (66.6 mmol), 12 ml of concentrated hydrochloric acid (144 mmol) which contains about 63% by weight of water, and 1.0 g of iodine (7.8 mmol as HI), and 100 ml of DMSO was stirred without heating for 24 hours in a 250 ml flask equipped with a reflux condenser. An amber-colored solution was obtained. This was seeded with L-cysteic acid-DMSO intermolecular compound. Two hundred fifty ml of acetone was added portion-wise, with stirring as crystallization progressed. The mixture was then iced to complete the precipitation. The product was filtered off, then reslurried with an 8% solution of DMSO in acetone. The product was again collected and finally rinsed with acetone. There was obtained 29.40 g of L-cysteic acid-DMSO intermolecular compound (89% yield). On taking the Mp, it sintered at 160° C. and then decomposed at about 180° C. Other forms of cysteic acid may also be used for seeding and seeding is not always necessary for precipitation.

The concentration of L-cystine employed in the above reaction is 0.666 M (i.e., 0.666 moles per liter of DMSO), and the concentration of HCl is 1.44 M. The concentration of $I_2$ as equivalent HI is 0.078 M, which gives a total catalyst concentration (HCL+$I_2$) of 1.518 M (per liter of DMSO). The water content is 4.96 M or about 5.0 moles per liter of DMSO.

The relatively high catalyst concentration and moderately high water concentration used in Example VI illustrate typical conditions which may be used when the sulfur-containing reactant includes a basic group such as an amino group. As illustrated, these conditions permitted the oxidation of L-cystine at room temperature. Similarly, L-cystine was also oxidized with HBr at a concentration of 1.1 M and a water content of 5.2 M. As stated previously, the term molar (M) as used herein refers to moles per liter of sulfoxide reactant.

EXAMPLE VII

Half a gram of anhydrous L-cysteic acid was treated with six ml of tetramethylene sulfoxide. Moderate heating was required to obtain solution. Addition of 10 ml of acetone caused precipitation of a crystalline product. After icing, this was filtered off and there was obtained 0.75 g of the appropriate intermolecular compound. This darkened and then decomposed at 215°–6° C. (capillary inserted into bath at 190°). Addition of more acetone to the mother liquor gave 0.05 g of a second crop, total, 0.80 g and yield, 98%.

|  | Calculated for $C_7H_{15}NO_6S_2$ | Found |
|---|---|---|
| Nitrogen | 5.13% | 4.87% |
| Sulfur | 23.46 | 23.61 |

Half a gram of the product was thoroughly and intimately mixed with two ml of methanol and allowed to stand 1½ hours with repeated mixing. A finer solid developed and this was filtered off and rinsed with more methanol. There was thus obtained 0.27 g of L-cysteic acid (yield, 87%). Mp 273°–5° C. with decomposition (capillary inserted at 265°).

EXAMPLE VIII

Half a gram of DL-homocysteic acid was treated with 2 ml of DMSO and the mixture allowed to stand for several days to attain complete solution. Addition of 15 ml of acetone caused a heavy syrup to develop. This could not be caused to crystallize. The supernatent liquid was decanted and the residue treated with 15 ml of fresh acetone. After a period, this was decanted and the residue again treated with 15 ml of fresh acetone. Removal of this left 0.96 g of residue, an aqueous solution of which would rapidly reduce permanganate while the acetone decants, particularly the last, would not. With further standing, the residue lost weight and became a mixture of a white precipitate and colorless syrup.

|  | Calculated for $C_6H_{15}NO_6S_2$ | Found | Atom Ratio |
|---|---|---|---|
| Nitrogen | 5.36% | 4.31% | 1 |
| Sulfur | 24.54 | 20.75 | 2 |

This evidence indicates that a one-to-one molecular compound was obtained which was, apparently, diluted by acetone; hence, the low nitrogen and sulfur values.

Similarly, one may substitute L-homocysteic acid for the DL form of this example to obtain the corresponding intermolecular compound.

EXAMPLE IX

Half a gram of DL-homocysteic acid was treated with 8 ml of tetramethylene sulfoxide. With moderate heating, a solution was obtained. Addition of 25 ml of acetone gave a heavy syrup which could not be induced to crystallize. The supernatent liquid was decanted and the residue treated with fresh acetone. After a period, this was decanted, and the residue again treated with fresh acetone. On removal of this, the residue DL-homocysteic acid-tetramethylene sulfoxide would rapidly reduce permanganate, whereas the last decanted acetone would not.

In a further aspect of the invention, I have formed intermolecular compounds of a sulfoxide with an amino acid which contains a sulfonic acid group and a carboxylic acid group, both as previously described, in which the molar ratio of the sulfoxide to the amino acid in the intermolecular compound may be varied within the range of about 0.2:1 to 1:1. Additionally, I have discovered a further way of forming intermolecular compounds by reacting the amino acid with the sulfoxide which is contained in a solvent having a moderate or low dielectric constant with the solvent being one in which neither the amino acid reactant nor the intermolecular compound product is particularly soluble, e.g., a solubility which is generally less than about one gram of amino acid or intermolecular compound per 100 grams of solvent. Alternatively, the intermolecular compound may be formed by directly contacting the sulfoxide with the amino acid in the absence of solvent, the amount of sulfoxide being insufficient to dissolve all the amino acid. Preferably, the solubility of either the amino acid or intermolecular compound in the solvent is rather limited with the solvent having a dielectric constant which may be about 26 or less. However, in my experiments, I have also conducted a reaction between the amino acid and the sulfoxide with the sulfoxide in solution in a solvent having a higher dielectric constant of about 37, such as N,N-dimethylformamide, which is also a generally poor solvent for the amino acid or intermolecular compound. Solvents which have a lower dielectric constant of about 26 or less include, for example, acetone, ethyl acetate, and chloroform.

In practice, the amino acid reactant may be stirred, slurried, or otherwise contacted with the solvent having a sulfoxide dissolved therein. The contact may be continued for an hour or longer, if desired, but contact with the amino acid reactant need be no longer than the time required for formation of the intermolecular compound. The exposed solvent may then be removed from the reaction medium by filtration or other means. This leaves the reaction solvent which contains what remains of the sulfoxide reactant, i.e., the concentration of the sulfoxide having been reduced as a result of the reaction. Additionally, the solid which is removed from the reaction medium undergoes a gain in weight as the result of the reaction with the solid containing the intermolecular compound that is formed.

Amino acid sulfoxide intermolecular compounds in which the molar ratio of sulfoxide to amino acid ranges from about 0.2:1 to 1:1 have the general characteristics of intermolecular compounds which contain the maximum quantity of the sulfoxide, i.e., a molar ratio of sulfoxide to amino acid of 1:1. Thus, the melting point or decomposition temperature of the exposed amino acid may be lowered as a result of the reaction. Additionally, a solution of the intermolecular compound in which the molar ratio of sulfoxide to amino acid ranges from about 0.20:1 to 1:1 will readily reduce permanganate because of the presence of sulfoxide in the intermolecular compound. In addition to forming an intermolecular compound, as described, the above reaction may be used in the removal of a dissolved sulfoxide from its solvent by absorption onto a solid amino acid (both as described previously).

To further illustrate the invention, the following examples are presented:

EXAMPLE X

Two grams of L-cysteic acid were added to 20 ml of acetone containing 1.5 ml (1.65 g) of dissolved DMSO. The mixture was allowed to stand with occasional stirring until the next day. The solid was then removed and rinsed with acetone and its dry weight was 2.79 g. In a melting point determination, it sintered at 160° C. and with further heating showed progressively increased effervescence, whereas the original L-cysteic acid did not decompose until about 270° C. When dissolved in water, the product decolorized added potassium permanganate solution quite rapidly in contrast with L-cysteic acid.

Essentially the same result was obtained when the L-cysteic acid was contacted with the DMSO-acetone solution for one hour or when L-cysteic acid monohydrate was used in place of L-cysteic acid. However, there was no increase in weight when the L-cysteic acid was contacted for one day with 20 ml of acetone containing 0.65 ml (0.71 g) of DMSO which illustrates that the formation of the intermolecular compound is dependent upon the concentration of the sulfoxide reactant in the solvent. Thus, depending upon the particular amino acid and the particular solvent, there can be a limiting concentration of the sulfoxide in the solvent which is necessary for formation of the intermolecular compound. This concentration may be readily determined in practice simply by weighing the removed solid after contact of the solution of the sulfoxide with the amino acid. If no weight gain is observed, then the sulfoxide concentration must be increased to form the intermolecular compound by absorption of the sulfoxide onto the amino acid.

EXAMPLE XI

Two grams of L-cysteic acid were added to 20 ml of DMF containing 1.5 ml (1.65 g) of DMSO in solution. The mixture was allowed to stand with occasional stirring until the next day. The solid was recovered and rinsed with a bit of DMF and then acetone. Its dry weight was 2.58 g.

EXAMPLE XII

Two grams of L-cysteic acid were contacted as above with 20 ml portions of toluene containing the amounts of dissolved DMSO shown in the accompanying table. Following recovery of the solid the weight was as shown:

| Amount of DMSO | Weight of Recovered Solid |
|---|---|
| 1.50 ml (1.65 g) | 2.84 g |
| 0.65 ml (0.71 g) | 2.57 g |
| 0.30 ml (0.33 g) | 2.23 g |

EXAMPLE XIII

The sulfoxide may also be absorbed from the vapor phase though generally, this is not a practical procedure because of the lower vapor pressure of sulfoxides at room temperature. This may be done at elevated temperatures as follows.

Two grams of L-cysteic acid were exposed to the vapors of DMSO in a chamber heated at 50° C. The increase in weight of the solid with time was as follows:

| Time (hours) | Weight (grams) |
|---|---|
| 6½ | 2.17 |
| 14 | 2.37 |
| 20½ | 2.52 |

An aqueous solution of the exposed solid decolorized added potassium permanganate solution almost instantaneously.

I claim:

1. An intermolecular compound of a saturated aliphatic amino acid of the empirical formula $C_nH_{2n-1}(NH_2)(CO_2H)(SO_3H)$, wherein n is a small whole number no greater than about 4, with a di-loweralkyl sulfoxide in which each alkyl group contains up to about 6 carbon atoms and each alkyl group may be the same or different and may be bonded together to form a ring structure, said amino acid having a solubility of about 4 grams or more per 100 milliliters of the sulfoxide at a temperature of about 25° C., the amino acid and sulfoxide being present in the intermolecular compound at a molar ratio of sulfoxide to said amino acid ranging from about 0.2:1 to 1:1.

2. The intermolecular compound of claim 1 wherein said molar ratio is 1:1.

3. The intermolecular compound of claim 1 wherein the amino acid is a cysteic acid or homocysteic acid and isomers thereof.

4. The intermolecular compound of claim 2 wherein the amino acid is a cysteic acid or homocysteic acid and isomers thereof.

5. The intermolecular compound of claim 2 wherein the sulfoxide is dimethyl sulfoxide.

6. The intermolecular compound of claim 2 wherein the sulfoxide is tetramethylene sulfoxide.

7. The intermolecular compound of claim 3 wherein the sulfoxide is dimethyl sulfoxide.

8. The intermolecular compound of claim 3 wherein the sulfoxide is tetramethylene sulfoxide.

9. The intermolecular compound of claim 1 wherein the sulfoxide is dimethyl sulfoxide.

10. The intermolecular compound of claim 1 wherein the sulfoxide is tetramethylene sulfoxide.

11. A process for separation or purification of a saturated aliphatic amino acid of the empirical formula $C_nH_{2n-1}(NH_2)(CO_2H)(SO_3H)$, wherein n is a small whole number no greater than about 4, said process comprising:

admixing the amino acid with a di-loweralkyl sulfoxide in which each alkyl group contains up to about 6 carbon atoms and each alkyl group may be the same or different and may be bonded together to form a ring structure and in which the amino acid has a solubility of about 4 grams or more per 100 ml. of the sulfoxide at a temperature of about 25° C. to obtain a solution;

precipitating the intermolecular compound containing the amino acid and sulfoxide in a 1:1 molar ratio from the excess sulfoxide, and liberating the amino acid from the intermolecular compound.

12. A process for forming an intermolecular compound containing a saturated aliphatic amino acid of the empirical formula $C_nH_{2n-1}(NH_2)(CO_2H)(SO_3)$, wherein n is a small whole number no greater than about 4, and a di-loweralkyl sulfoxide in which each alkyl group contains up to about 6 carbon atoms and each alkyl group may be the same or different and may be bonded together to form a ring structure at a molar ratio of sulfoxide to amino acid ranging from about 0.2:1 to 1:1, said sulfoxide being one in which the amino acid is soluble to the extent of about 4 grams or more per 100 ml. of sulfoxide, said process comprising:

contacting the amino acid with the di-loweralkyl sulfoxide at a temperature of about 25° C., and separating said intermolecular compound from said sulfoxide.

13. The process of claim 12 wherein an excess quantity of said sulfoxide is present in the reaction medium.

14. The process of claim 12 wherein said sulfoxide is in solution in a solvent having a dielectric constant of about 26 or less in which said amino acid and intermolecular compound are sparingly soluble.

15. The process of claim 12 wherein said amino acid is dissolved in said sulfoxide and the intermolecular compound formed therefrom has a molar ratio of sulfoxide to amino acid of 1:1.

* * * * *